United States Patent
Cho et al.

(10) Patent No.: US 9,664,628 B2
(45) Date of Patent: May 30, 2017

(54) INSPECTION METHOD

(75) Inventors: Soo-Young Cho, Seoul (KR); Bong-Ha Hwang, Seoul (KR); Min-Young Kim, Seoul (KR)

(73) Assignees: KOH YOUNG TECHNOLOGY INC., Seoul (KR); KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 1240 days.

(21) Appl. No.: 13/302,895

(22) Filed: Nov. 22, 2011

(65) Prior Publication Data

US 2012/0130666 A1 May 24, 2012

(30) Foreign Application Priority Data

Nov. 23, 2010 (KR) ........................ 10-2010-0117000

(51) Int. Cl.
*G01N 21/956* (2006.01)

(52) U.S. Cl.
CPC ..... *G01N 21/95684* (2013.01); *G01N 21/956* (2013.01); *G01N 2021/95638* (2013.01)

(58) Field of Classification Search
CPC ........... G01N 21/956; G01N 21/95684; G01N 2021/95638
USPC ......................................................... 702/87
See application file for complete search history.

(56) References Cited

U.S. PATENT DOCUMENTS

| | | | |
|---|---|---|---|
| 5,575,076 A | 11/1996 | Creeden | |
| 7,490,019 B2 | 2/2009 | Fukumoto et al. | |
| 2002/0113234 A1* | 8/2002 | Okuda et al. | 257/48 |
| 2002/0145733 A1* | 10/2002 | Wada et al. | 356/237.2 |
| 2006/0239536 A1* | 10/2006 | Shibuya et al. | 382/149 |
| 2007/0172111 A1* | 7/2007 | Ikeda | 382/149 |
| 2010/0246931 A1* | 9/2010 | Kim et al. | 382/141 |

FOREIGN PATENT DOCUMENTS

| | | |
|---|---|---|
| CN | 1746667 | 3/2006 |
| CN | 101726262 | 6/2010 |
| CN | 101852745 | 10/2010 |

(Continued)

*Primary Examiner* — Gregory J Toatley
*Assistant Examiner* — Yoshihisa Ishizuka
(74) *Attorney, Agent, or Firm* — Kile Park Reed & Houtteman PLLC (57) ABSTRACT

In order to inspect a board, a measurement area is set on a board, and reference data and measurement data of the measurement area are acquired. Then, a conversion condition is established for the measurement area, and a conversion relation is acquired according to a distortion degree between reference data and measurement data. Thereafter, validity of the conversion relation is verified by using at least one of verifying that a comparison feature object satisfies the conversion relation, verifying that a verification feature object selected from feature objects satisfies the conversion relation and verifying that a pad formed on the board satisfies the conversion relation. Then, the conversion condition is confirmed, and an inspection area for inspecting a measurement target is set according to the confirmed conversion condition. Thus, an inspection area may be correctly set so that distortion is compensated for.

7 Claims, 5 Drawing Sheets

(56) References Cited

FOREIGN PATENT DOCUMENTS

| | | |
|---|---|---|
| DE | 44-38-278 | 4/1995 |
| DE | 195-00-382 | 7/1995 |
| DE | 199-10-412 | 8/1999 |
| DE | 695-02-276 | 7/2005 |
| DE | 10-2008-031-240 | 1/2010 |
| EP | 1 413 850 | 4/2004 |
| EP | 1 462 997 | 9/2004 |
| JP | 2008-185514 | 8/2008 |
| JP | 2008-298461 | 12/2008 |
| JP | 2010-014504 | 1/2010 |
| JP | 2010-237210 | 10/2010 |
| TW | 480424 | 3/2002 |
| TW | 200532162 | 10/2005 |
| TW | 201018331 | 5/2010 |
| WO | 2009/097066 | 8/2009 |
| WO | 2009/140461 | 11/2009 |

\* cited by examiner

FIG. 5

INSPECTION METHOD

CROSS REFERENCE TO RELATED APPLICATION

This application claims priority from and the benefit of Korean Patent Applications No. 2010-117000 filed on Nov. 23, 2010, which is hereby incorporated by reference for all purposes as if fully set forth herein.

BACKGROUND OF THE INVENTION

Field of the Invention

Exemplary embodiments of the present invention relate to an inspection method. More particularly, exemplary embodiments of the present invention relate to an inspection method for a board.

Discussion of the Background

Generally, at least one printed circuit board (PCB) is employed in an electronic device, is and various circuit elements such as a circuit pattern, a connection pad part, a driver chip electrically connected to the connection pad part, etc. are mounted on the PCB.

A shape measurement apparatus is typically used to check whether the various circuit elements are formed or configured good or not on the printed circuit board.

In a conventional shape measurement apparatus, a predetermined inspection area is set to inspect whether circuit elements are formed good or not in the inspection area. In a conventional method of setting an inspection area, an area, in which circuit elements are theoretically located, is simply set as an inspection area.

When the inspection area is set at a correct location, a measurement of a desired circuit element is performed well. However, in a measurement target such as a PCB, distortion such as warpage, contortion, etc. of a base board may be generated. Thus, in the conventional method of setting an inspection area, the inspection area is not correctly set at a desired location, and a location corresponding to an image acquired in a camera of an image capturing part is a little different from a location where a circuit element actually exists.

Thus, an inspection area is required to set to compensate for the distortion of the measurement target.

SUMMARY OF THE INVENTION

Exemplary embodiments of the present invention provide an inspection apparatus capable of setting an inspection area, in which distortion of a measurement target is compensated for, and more correctly defining a conversion relation used in compensating for distortion.

Additional features of the invention will be set forth in the description which follows, and in part will be apparent from the description, or may be learned by practice of the invention.

An exemplary embodiment of the present invention discloses an inspection method. The inspection method includes setting a measurement area on a board, acquiring reference data and measurement data of the measurement area, establishing a conversion condition including a comparison feature object for the measurement area, acquiring a conversion relation according to a distortion degree by comparing reference data and measurement data corresponding to the comparison feature object with each other, verifying validity of the conversion relation by using at least one of a first verification method of verifying that the comparison feature object satisfies the conversion relation, a second verification method of verifying that a verification feature object selected from feature objects except for the comparison feature object satisfies the conversion relation and a third verification method of verifying that a pad corresponding to an inspection target formed on the board satisfies the conversion relation, confirming the conversion condition in case that the conversion relation is judged to be valid, and setting an inspection area for inspecting a measurement target according to the confirmed conversion condition.

For example, verifying validity of the conversion relation may be performed in order of the first verification method, the second verification method and the third verification method.

In an exemplary embodiment, in case that the conversion relation is not valid as a result of verification of the validity of the conversion relation, the inspection method may further include changing the conversion condition, and repeating the step of acquiring the conversion relation and the following steps.

For example, the conversion condition may further include at least one of a coordinate conversion model and an illumination setting of an illumination device.

In an exemplary embodiment, in case that the conversion relation is not valid as a result of verification of the validity of the conversion relation, the inspection method may further include repeating the step of acquiring the conversion relation and the following steps, by using a conversion condition of an adjacent measurement area adjacent to the measurement area.

For example, the set measurement area may be plural, and the conversion condition may be established for each measurement area.

Another exemplary embodiment of the present invention discloses an inspection method. The inspection method includes setting a measurement area on a board, acquiring reference data and off-line measurement data of the measurement area, establishing a conversion condition including a comparison feature object for the measurement area, acquiring an off-line conversion relation according to a predetermined coordinate conversion model by comparing reference data and off-line measurement data corresponding to the comparison feature object with each other, verifying validity of the off-line conversion relation by using at least one of a first verification method of verifying that the comparison feature object satisfies the off-line conversion relation, a second verification method of verifying that a verification feature object selected from feature objects except for the comparison feature object satisfies the off-line conversion relation and a third verification method of verifying that a pad corresponding to an inspection target formed on the board satisfies the off-line conversion relation, confirming the conversion condition in case that the off-line conversion relation is judged to be valid, and setting an inspection area for inspecting a measurement target according to the confirmed conversion condition.

Still another exemplary embodiment of the present invention discloses an inspection method. The inspection method includes setting a measurement area on a board, acquiring reference data of the measurement area, acquiring in-line measurement data of the measurement area, acquiring an in-line conversion relation according to a predetermined coordinate conversion model by comparing reference data and in-line measurement data corresponding to the comparison feature object with each other, verifying validity of the in-line conversion relation by using at least one of a first verification method of verifying that the comparison feature object satisfies the in-line conversion relation, and a second verification method of verifying that a verification feature object selected from feature objects except for the comparison feature object satisfies the off-line conversion relation, and setting an inspection area for inspecting a measurement target by using the in-line conversion condition in case that the in-line conversion relation is judged to be valid.

For example, the comparison feature object and the verification feature object may be defined as a feature block by a block unit.

Still another exemplary embodiment of the present invention discloses an inspection method. The inspection method includes setting a measurement area on a board, acquiring reference data and measurement data of the measurement area, establishing a conversion condition including at least two feature objects for the measurement area, acquiring a conversion relation according to a distortion degree by comparing reference data and measurement data corresponding to at least one of the feature objects with each other, and verifying validity of the conversion relation.

For example, the feature object may include a comparison feature object used to acquire the conversion relation and a verification feature object except for the comparison feature object.

In an exemplary embodiment, verifying validity of the conversion relation may be performed by verifying that at least one of a comparison feature object used to acquire the conversion relation, a verification feature object except for the comparison feature object, and a pad formed on the board satisfies the conversion relation.

In an exemplary embodiment, in case that an in-line inspection, verifying validity of the conversion relation may be performed by verifying that at least one of a comparison feature object used to acquire the conversion relation, and a verification feature object except for the comparison feature object satisfies the conversion relation.

In an exemplary embodiment, in case that an off-line inspection, verifying validity of the conversion relation may be performed by verifying that at least one of a comparison feature object used to acquire the conversion relation, a verification feature object except for the comparison feature object, and a pad formed on the board satisfies the conversion relation.

In case that the conversion relation is not valid as a result of verification of the validity of the conversion relation, the inspection method may further include changing the conversion condition, and repeating the step of acquiring the conversion relation and the following step or steps.

For example, the conversion condition may further include at least one of a coordinate conversion model and an illumination setting of an illumination device.

According to the present invention, feature objects in a measurement area set on a board are used for a comparison feature object and a verification feature object, and a conversion relation between reference data and measurement data is established and verified, to thereby more correctly set an inspection area.

In addition, proper verifications may be performed for each step by applying different verification criterion for in-line and off-line.

In addition, a work such as an inspection of components may be performed based on the measurement area set as described above, to thereby more correctly judge whether the board is good or bad.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments of the invention are described herein with reference to cross-sectional illustrations that are schematic illustrations of idealized example embodiments (and intermediate structures) of the present invention. As such, variations from the shapes of the illustrations as a result, for example, of manufacturing techniques and/or tolerances, are to be expected. Thus, example embodiments of the present invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, exemplary embodiments of the present invention will be described in detail with reference to the accompanying drawings.

Figure 1:
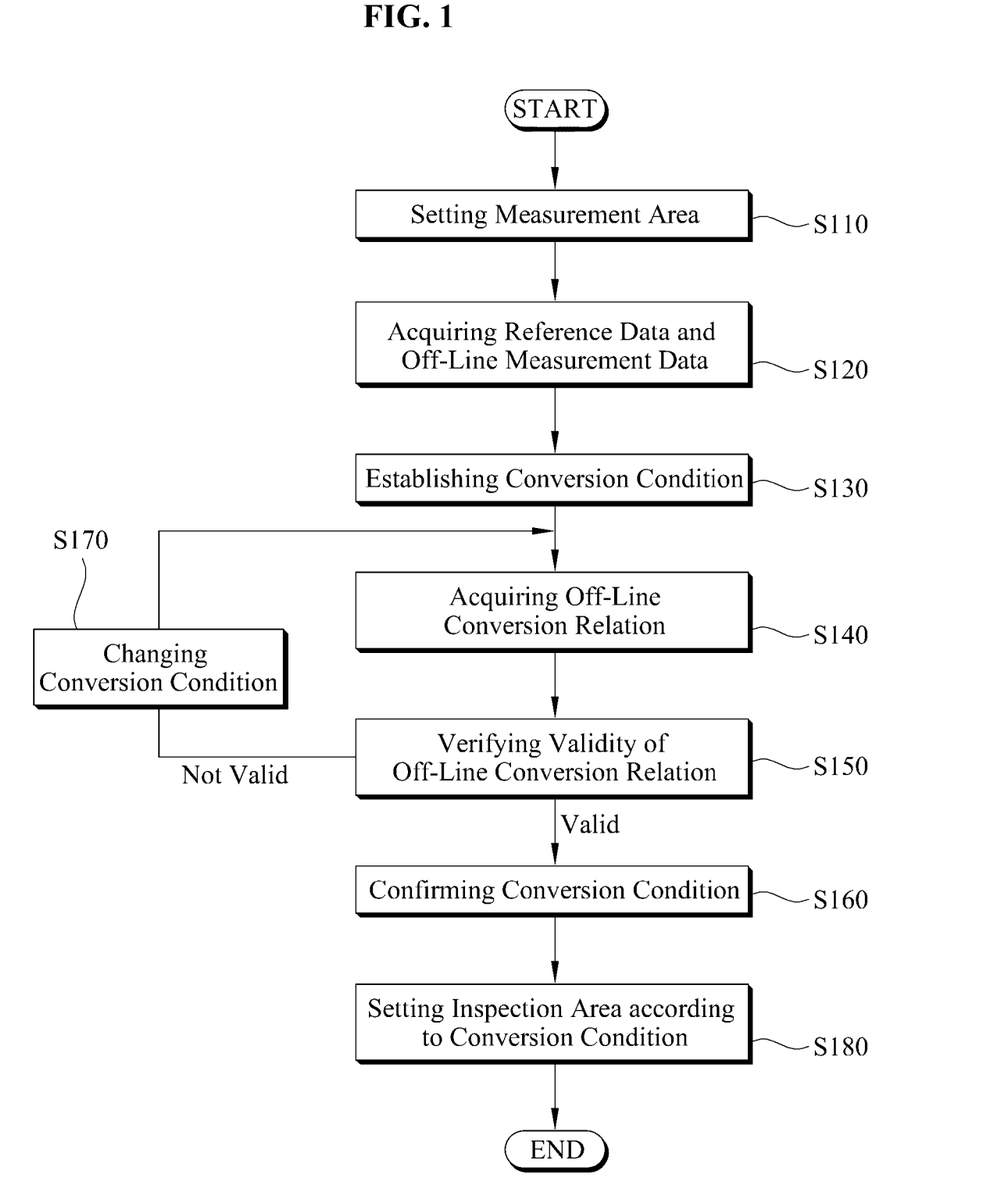
FIG. 1 is a flow chart illustrating an inspection method according to an exemplary embodiment of the present invention.
Figure 2:
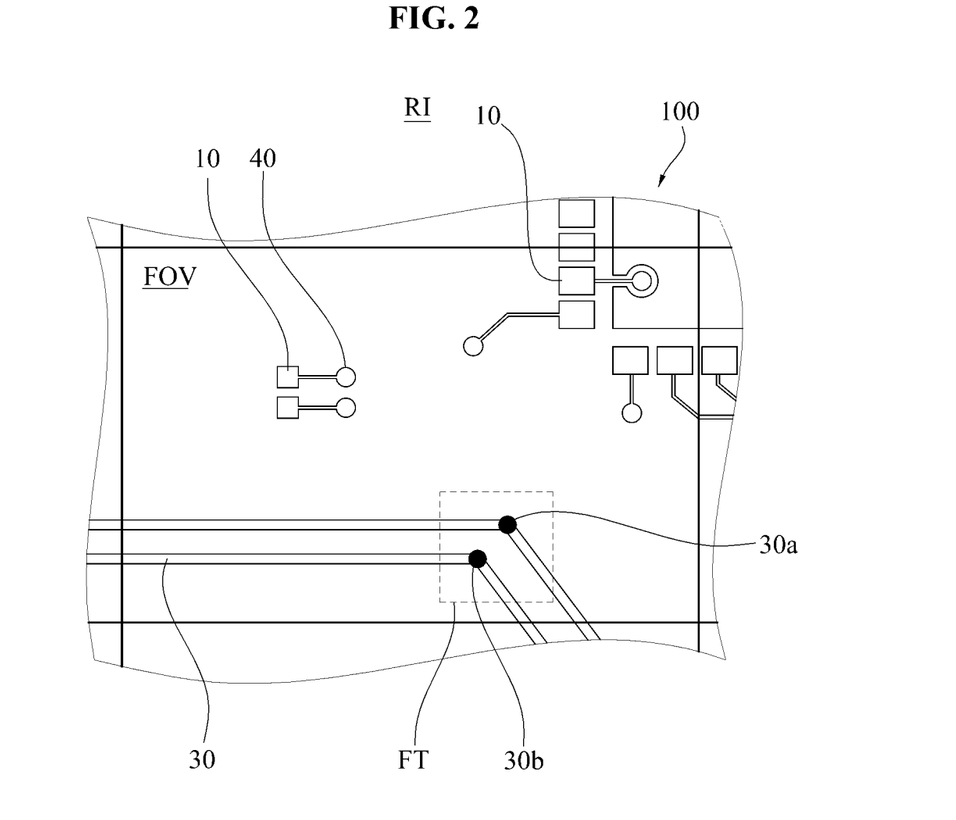
FIG. 2 is a plan view illustrating an example of reference data in the inspection method shown in FIG. 1.

FIG. 1 is a flow chart illustrating an inspection method according to an exemplary embodiment of the present invention. FIG. 2 is a plan view illustrating an example of reference data in the inspection method shown in FIG. 1.

Referring to FIGS. 1 and 2, in order to set an inspection area in which distortion is compensated for according to an exemplary embodiment of the present invention, firstly a measurement area FOV is set on a board 100 in step of S110.

The measurement area FOV indicates a predetermined area that is set on the board 100 so as to inspect whether the board is bad or not, and may be defined, for example, based on a "field of view" of a camera installed in an inspection apparatus such as a three-dimensional shape measurement apparatus.

Then, reference data RI and off-line measurement data of the measurement area FOV are acquired in step of S120.

The reference data RI may correspond to, for example, a theoretical plan image of the board 100 as shown in FIG. 2.

In an exemplary embodiment, the reference data RI may be obtained from CAD information or gerber information in which a shape of the board 100 is recorded. The CAD information or the gerber information may include design information of the board, and typically include configuration information of a pad 10, a circuit pattern 30, a hole pattern 40, etc.

In another exemplary embodiment, the reference data RI may be acquired from learning information that is obtained in a learning mode. The learning mode may be realized by processes, for example, such as searching board information in a database, learning a bare board in case that the board information is not in the database, and storing the board information in the database after the board information is produced by learning the bare board. That is, in the learning mode, a bare board of a PCB is learned and design reference information of the PCB is acquired, and the reference data RI may be acquired by obtaining the learning information through the learning mode.

The off-line measurement data may correspond to data acquired by measuring the board 100 before forming a component, etc. on the board 100 as shown in FIG. 2, and may be, for example, an image for the board 100 corresponding to the reference data RI, which is actually captured by using an inspection apparatus such as a three-dimensional shape measurement apparatus. The off-line measurement data has a similar image to the reference data RI shown in FIG. 2. However, the off-line measurement data is a little distorted in comparison with the reference data RI, due to warpage, contortion, etc. of the board 100.

In an exemplary embodiment, the off-line measurement data may be acquired by providing light onto the measurement area FOV using the illumination section of the inspection apparatus, and capturing an image reflected by the provided light using a camera installed in the inspection apparatus. Alternatively, the off-line measurement data may be acquired by projecting grating pattern light onto the measurement area FOV using a grating pattern projecting section of the inspection apparatus, capturing an image reflected by the projected grating pattern light to obtain data for a three-dimensional shape, and averaging the data for the three-dimensional shape.

Thereafter, a conversion condition is established for the measurement area FOV in step of S130.

The conversion condition may be predetermined for acquiring an off-line conversion relation, which will be described later, and a conversion relation according to change between the reference data and the off-line measurement data is acquired under the predetermined conversion condition.

The set measurement area FOV may be plural, and, in an exemplary embodiment, the conversion condition may be established for each measurement area.

The conversion condition includes a comparison feature object, and the comparison feature object may be properly selected from various feature objects according to shape, location, distribution, etc. to form the conversion condition.

The comparison feature object may be used for a comparison reference so as to acquire a conversion relation between the reference data RI and the off-line measurement data, which will be described later. That is, the conversion relation is defined by using a degree by which the comparison feature object is changed between the reference data RI and the off-line measurement data, due to distortion of the board 100.

The comparison feature object may include an object having a predetermined shape located at a specific coordinate in the reference data RI and the off-line measurement data. For example, the comparison feature object may include a hole pattern, a corner portion of a bent circuit pattern, etc. formed on the board 100, and a conversion relation, which will be described later, may be acquired by comparing the reference data RI with the off-line measurement data based on a coordinate of a central point of the hole pattern and a coordinate of a corner point of the bent circuit pattern.

Alternatively, the comparison feature object may be, as shown in FIG. 2, defined as a feature block FT by a block unit. In case of defining the comparison feature object as a feature block, since the reference data RI and the off-line measurement data may be compared with each other based on various shapes included in the feature block FT, the reference data RI and the off-line measurement data may be accurately compared with each other.

Since the comparison feature object is used as a comparison reference to acquire a conversion relation between the reference data RI and the off-line measurement data, it is desirable to accurately establish the comparison feature object in the reference data RI and the off-line measurement data. For the above accurate establishment, it may occur that no object or few objects selectable as the comparison feature object exist in the measurement area FOV. Thus, in order to secure sufficient comparison feature objects, the comparison feature objects may be extracted from adjacent measurement areas adjacent to the measurement area FOV.

The conversion condition may further include a coordinate conversion model.

The off-line measurement data is distorted due to warpage, contortion, etc. of the board in comparison with the reference data RI corresponding to theoretical reference information. The conversion relation may be established between the reference data RI and the off-line measurement data, according to a distortion degree that expresses a degree of the distortion. The conversion relation may be expressed in various forms of mathematical models, and the mathematical models correspond to the coordinate conversion model.

The coordinate conversion model and the conversion relation will be described later in detail.

The conversion condition may further include an illumination setting of an inspection apparatus, for example, such as a three-dimensional shape measurement apparatus. In other words, since the off-line measurement data may be variable according to illumination of an inspection apparatus, the conversion condition may include an illumination setting. For example, the illumination setting may include an illuminated angle, a color, a brightness, etc. for acquiring the off-line measurement data.

Then, reference data and off-line measurement data corresponding to the comparison feature object is compared with each other, and an off-line conversion relation is acquired according to the distortion degree between the reference data and the off-line measurement data in step of S140.

The off-line conversion relation may be determined by using at least one of a location change, a slope change, a size change and a transformation degree, which are acquired by comparing the reference data RI and the measurement data PI corresponding to the comparison block with each other.

For example, the conversion relation may be expressed as Equation 1 by using the coordinate conversion model.

$$P_{CAD} f(tm) = P_{real} \qquad \text{Equation 1}$$

In Equation 1, $P_{CAD}$ is a coordinate of a target in CAD information or gerber information, i.e., a coordinate in the reference data RI, f(tm) corresponds to the coordinate conversion model serving as a conversion matrix or a transfer matrix, and and $P_{real}$ is a coordinate of the target in the off-line measurement data, which is acquired by a camera. When the theoretical coordinate $P_{CAD}$ in the reference data RI and the real coordinate $P_{real}$ in the off-line measurement data are found, the conversion matrix may be known.

For example, the conversion matrix may include a coordinate conversion matrix according to an affine conversion or a perspective conversion, in which point-to-point relation is expressed as a first-order form in an n-dimensional space. In order to define the coordinate conversion matrix, the number of the feature objects may be properly established, for example, more than or equal to three in case of an affine conversion and more than or equal to four in case of a perspective conversion.

The coordinate conversion model serves as the conversion condition, and is previously established in any one model. The coordinate conversion model may be modified to other coordinate conversion model according to a verification process, which will be described later.

Thereafter, validity of the off-line conversion relation is verified in step of S150.

The verification method of verifying the validity of the off-line conversion relation includes at least one of a first verification method, a second verification method and a third verification method.

The first verification method corresponds to a method of verifying that the comparison feature object satisfies the off-line conversion relation.

The comparison feature object corresponds to a feature object used to acquire the off-line conversion relation, but a great error may occur in applying the acquired off-line conversion relation. Thus, in case that the error exceeds a predetermined tolerance range, the conversion relation may be judged to be invalid.

The second verification method corresponds to a method of verifying that a verification feature object selected from feature objects except for the comparison feature object satisfies the off-line conversion relation.

Since the verification feature object corresponds to a feature object not used to acquire the off-line conversion relation, the off-line conversion relation may be judged to have greater reliability, when an error is not very great in applying the verification feature object to the acquired off-line conversion relation. Thus, the conversion relation may be judged to be valid, when the error in applying the verification feature object does not exceed the predetermined tolerance range.

For example, the verification feature object may be extracted simultaneously with extraction of the comparison feature object, and alternatively, the verification feature object may be newly extracted when changing the conversion condition, which will be described later.

The third verification method corresponds to a method of verifying that a pad corresponding to an inspection target formed on the board satisfies the off-line conversion relation.

Even though the conversion relation is judged to be valid through the first and second verification methods, in case that an inspection target is, for example, a pad, on which solder will be formed, it is difficult that the inspection result has reliability when the pad does not satisfies the off-line conversion relation. Thus, when the pad corresponding to a real inspection target, serves as the feature object, the conversion relation may be judged to be invalid in case that the pad exceeds to the predetermined tolerance range.

For example, the error may be calculated by difference between a real coordinate of the feature object and an expected coordinate after applying the conversion relation to the reference data.

The reliability of the acquired off-line conversion relation may be secured through the verification methods as described above.

The first, second and third verification methods are selectively or wholly used. In case that at least two of the first, second and third verification methods are used, the methods may preferably be performed in order of the first verification method, the second verification method and the third verification method.

Figure 3:
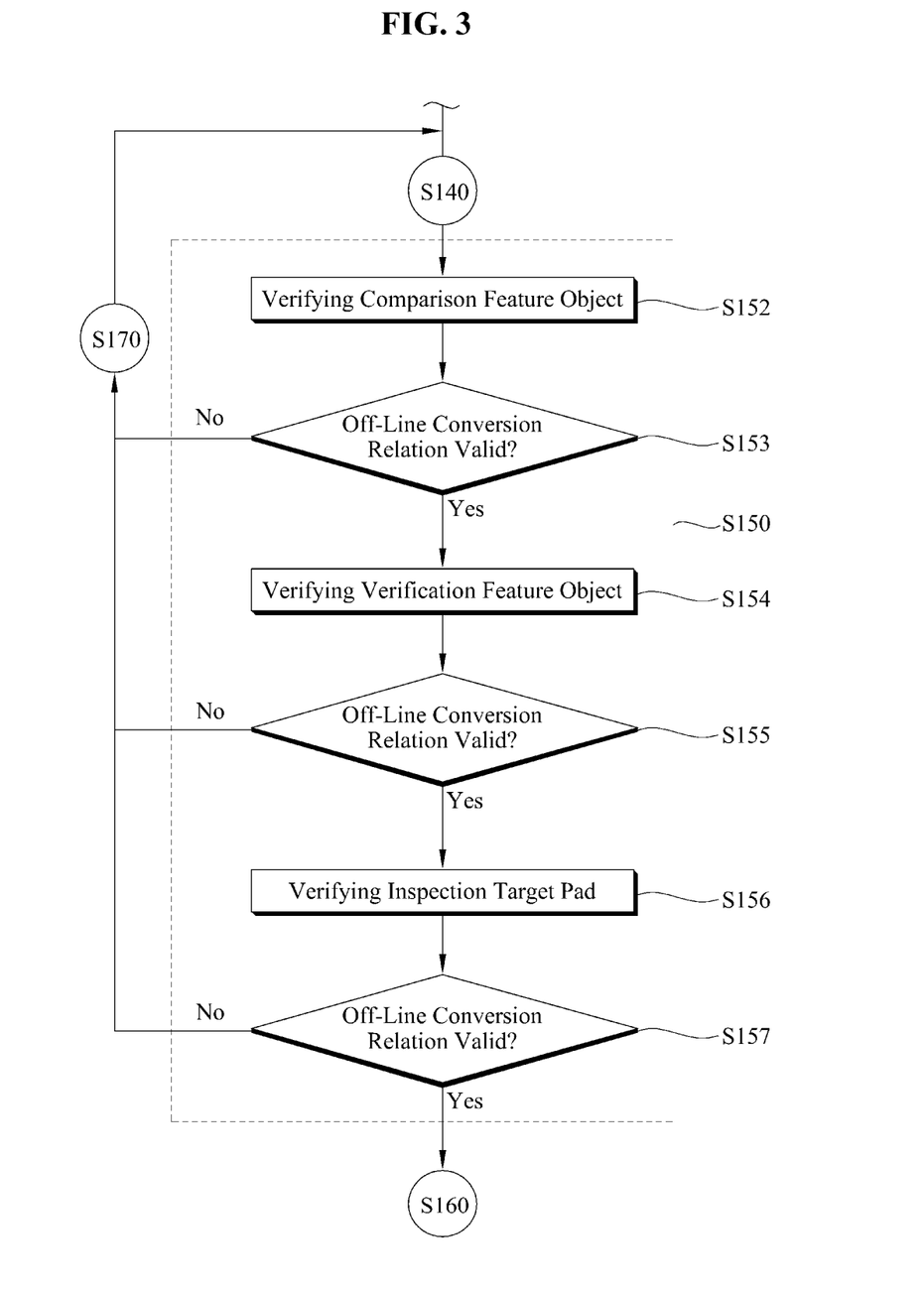
FIG. 3 is a flow chart illustrating an exemplary embodiment of verifying validity of an off-line conversion relation in FIG. 1.

FIG. 3 is a flow chart illustrating an exemplary embodiment of verifying validity of an off-line conversion relation in FIG. 1.

Referring to FIGS. 1 and 3, firstly, the comparison feature object is verified according to the first verification method in step of S152, and it is judged whether the off-line conversion relation is valid or not in step of S153. When the off-line conversion relation is not valid, the conversion condition is changed in step of S170, and thereafter it is returned to the step of acquiring the off-line conversion relation (S140).

Then, when the off-line conversion relation is valid, the verification feature object is verified according to the second verification method in step of S154, and it is judged whether the off-line conversion relation is valid or not in step of S155. When the off-line conversion relation is not valid, the conversion condition is changed in step of S170, and thereafter it is returned to the step of acquiring the off-line conversion relation (S140).

Thereafter, when the off-line conversion relation is valid, the pad corresponding to an inspection target is verified according to the third verification method in step of S154, and it is judged whether the off-line conversion relation is valid or not in step of S155. When the off-line conversion relation is not valid, the conversion condition is changed in step of S170, and thereafter it is returned to the step of acquiring the off-line conversion relation (S140).

Then, in case that the off-line conversion relation is judged to be valid, the conversion condition is confirmed in step of S160.

In case that the conversion relation is not valid as a result of verification of the validity of the conversion relation, as described above, after the conversion condition is changed in step of S170, it is returned to the step of acquiring the off-line conversion relation (S140), and thereafter the following steps are repeated.

Thereafter, an inspection area for inspecting a measurement target in the measurement area FOV is set by compensating for distortion, according to the confirmed conversion condition in step of S180.

Figure 4:
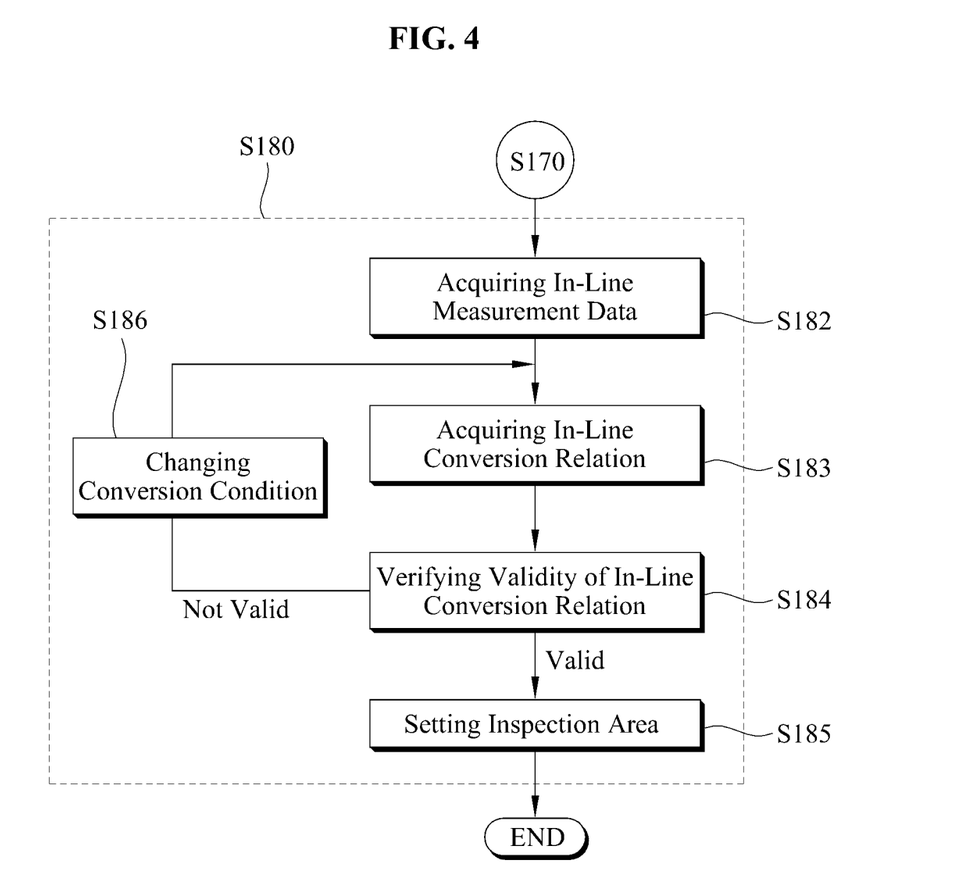
FIG. 4 is a flow chart illustrating setting an inspection area according to an exemplary embodiment of the present invention.

FIG. 4 is a flow chart illustrating setting an inspection area according to an exemplary embodiment of the present invention.

Referring to FIGS. 2 and 4, firstly, in-line measurement data of the measurement area FOV are acquired in step of S182.

The in-line measurement data may correspond to data acquired by measuring a real PCB, in which a component mounted on the board 100, a terminal 22, a polar indication 24 formed at the component, a circuit pattern, a hole, etc. exist, and may be, for example, an image for a PCB is in which a component, a pattern, etc. are formed on the board 100 corresponding to the reference data RI, which is actually captured by using an inspection apparatus such as a three-dimensional shape measurement apparatus. The in-line measurement data has a similar image to the reference data RI shown in FIG. 2. However, the in-line measurement data is a little distorted in comparison with the reference data RI, due to warpage, contortion, etc. of the board 100.

A method of acquiring the in-line measurement data is substantially the same as the method of acquiring the off-line measurement data, and thus further description will be omitted.

Then, reference data corresponding to the comparison feature object and in-line measurement data are compared with each other, and an in-line conversion relation is acquired according to a distortion degree between the reference data and the in-line measurement data in step of S183.

A method of acquiring the in-line conversion relation is substantially the same as the method of acquiring the off-line conversion relation except for being performed in-line, and thus further description will be omitted.

Thereafter, validity of the in-line conversion relation is verified in step of S184.

The method of verifying the validity of the in-line conversion relation includes at least one of a fourth verification method and a fifth verification method.

The fourth verification method and the fifth verification method are substantially the same as the first verification method and the second verification method, respectively, except for being performed in-line and using a conversion condition of an adjacent measurement area in case that the in-line conversion relation is not valid, and thus further description will be omitted.

Hereinafter, an exemplary embodiment of verifying the validity of the in-line conversion relation will be described in detail with reference to the accompanying drawings.

Figure 5:
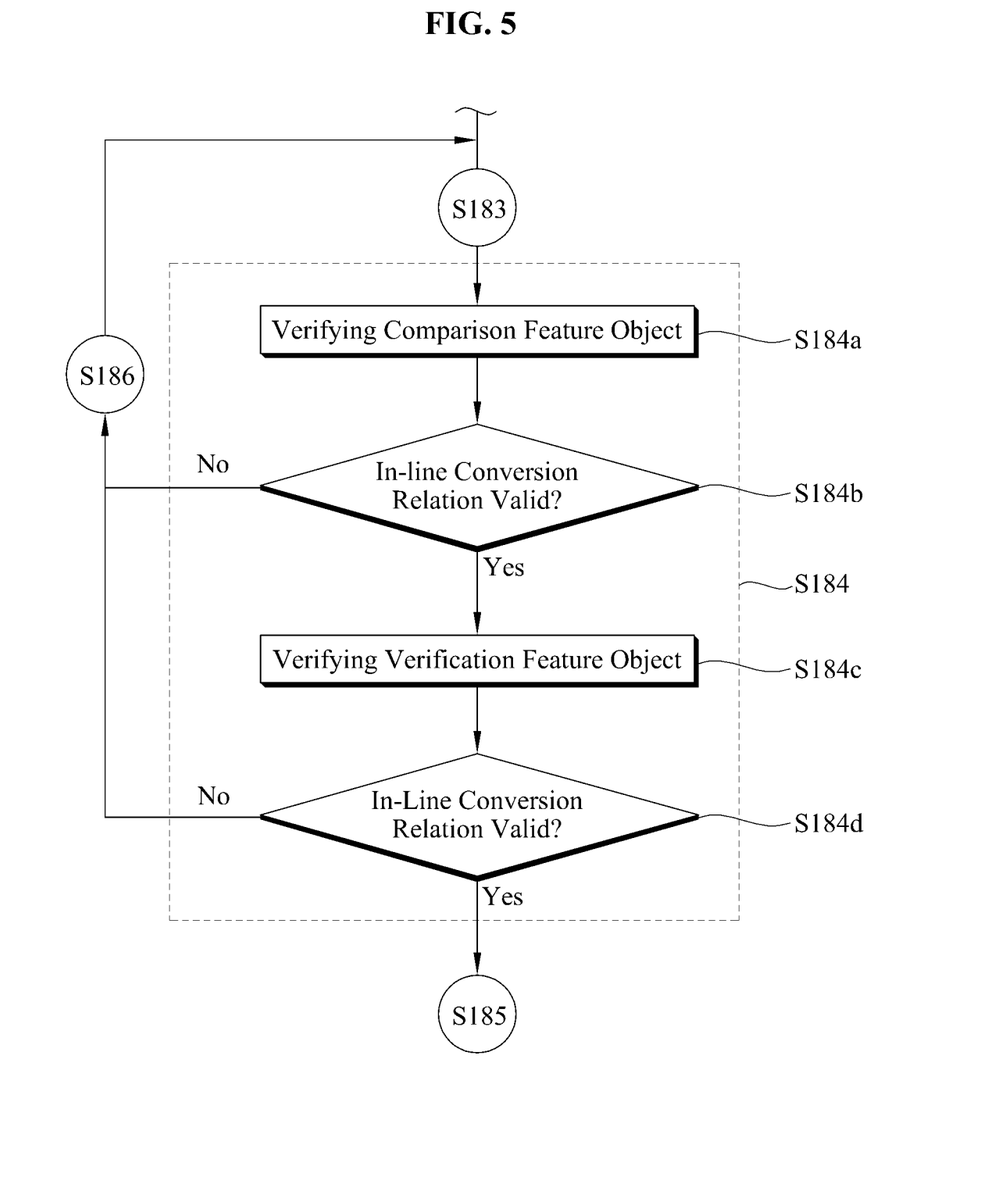
FIG. 5 is a flow chart illustrating an exemplary embodiment of verifying validity of an in-line conversion relation in FIG. 4.

FIG. 5 is a flow chart illustrating an exemplary embodiment of verifying validity of an in-line conversion relation in FIG. 4.

Referring to FIGS. 4 and 5, firstly, the comparison feature object is verified according to the fourth verification method in step of S184a, and it is judged whether the in-line conversion relation is valid or not in step of S184b. When the in-line conversion relation is not valid, the conversion condition is changed in step of S186, and thereafter it is returned to the step of acquiring the in-line conversion relation (S183). The conversion condition may be changed by using a conversion condition of an adjacent measurement area. When the adjacent measurement area is plural, the conversion condition may be changed by selecting one of the adjacent measurement areas or using an average of two or more adjacent measurement areas.

Then, when the in-line conversion relation is valid, the verification feature object is verified according to the fifth verification method in step of S184c, and it is judged whether the in-line conversion relation is valid or not in step of S184d. When the in-line conversion relation is not valid, the conversion condition is changed in step of S186, and thereafter it is returned to the step of acquiring the in-line conversion relation (S183). The conversion condition may be changed by using a conversion condition of an adjacent measurement area. When the adjacent measurement area is plural, the conversion condition may be changed by selecting one of the adjacent measurement areas or using an average of two or more adjacent measurement areas.

Then, in case that the in-line conversion relation is judged to be valid, the inspection area is set by using the in-line conversion relation in step of S185.

In case that the in-line conversion relation is not valid as a result of verification of the validity of the in-line conversion relation, as described above, after the conversion condition is changed by using a conversion condition of an adjacent measurement area adjacent to the measurement area FOV in step of S186, it is returned to the step of acquiring the in-line conversion relation (S183), and thereafter the following steps are repeated.

According to the above, feature objects in a measurement area set on a board are used for a comparison feature object and a verification feature object, and a conversion relation between reference data and measurement data is established and verified, to thereby more correctly set an inspection area.

In addition, proper verifications may be performed for each step by applying different verification criterion for in-line and off-line.

In addition, a work such as an inspection of components may be performed based on the measurement area set as described above, to thereby more correctly judge whether the board is good or bad.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. An inspection method comprising:
    setting, by a central processing unit, a measurement area on a board, the measurement area including a comparison feature object and a verification feature object;
    acquiring, by the central processing unit, reference data and measurement data of the measurement area;
    establishing, by the central processing unit, a conversion condition for the measurement area;
    acquiring, by the central processing unit, a conversion relation by comparing reference data and measurement data corresponding to the comparison feature object, wherein the conversion relation includes a distortion between the reference data and the measurement data corresponding to the comparison feature object;
    applying, by the central processing unit, the conversion relation with respect to reference data and measurement data corresponding to the verification feature object to obtain an error;
    verifying, by the central processing unit, validity of the conversion relation by determining whether the error exceeds a predetermined tolerance range;
    confirming, by the central processing unit, the conversion condition when the validity of the conversion relation is verified and the error does not exceed the predetermined tolerance range; and
    setting, by the central processing unit, an inspection area by compensating the distortion according to the confirmed conversion condition;
    inspecting, by the central processing unit, the board based on the inspection area to correctly judge whether the board is good or bad.

2. The inspection method of claim 1, further comprising verifying, by a central processing unit, validity of the acquired conversion relation by using at least one of a first verification method of verifying that the verification feature object selected from feature objects except for the comparison feature object satisfies the conversion relation, and
    a second verification method of verifying that a pad corresponding to an inspection target formed on the board satisfies the conversion relation, and verifying validity of the conversion relation is performed in order of the first verification method and the second verification method.

3. The inspection method of claim 1, in case that the conversion relation is not valid as a result of verification of the validity of the conversion relation, further comprising:
    changing the conversion condition; and
    repeating acquiring the conversion relation, confirming the conversion condition, and setting the inspection area.

4. The inspection method of claim 1, wherein the conversion condition further includes at least one of a coordinate conversion model and an illumination setting of an illumination device.

5. The inspection method of claim 1, wherein in case that the conversion relation is not valid as a result of verification of the validity of the conversion relation,
    further comprising repeating acquiring the conversion relation, confirming the conversion condition, and setting the inspection area, by using a conversion condition of an adjacent measurement area adjacent to the measurement area.

6. The inspection method of claim 1, wherein the set measurement area is plural, and the conversion condition is established for each measurement area.

7. The inspection method of claim 1, wherein the comparison feature object and the verification feature object are defined as a feature block by a block unit.

* * * * *